US00PP36463P3

(12) United States Plant Patent
Schoone

(10) Patent No.: US PP36,463 P3
(45) Date of Patent: Feb. 18, 2025

(54) ***PHALAENOPSIS* PLANT NAMED 'Snoozer'**

(50) Latin Name: *Phalaenopsis hybrida*
Varietal Denomination: Snoozer

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 18/625,182

(22) Filed: Apr. 2, 2024

(65) Prior Publication Data

US 2024/0334856 P1 Oct. 3, 2024

Related U.S. Application Data

(60) Provisional application No. 63/456,505, filed on Apr. 2, 2023.

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
See application file for complete search history.

(56) References Cited

PUBLICATIONS https://online.plantvarieties.eu/publicConsultationDetails?registerId=20230528&denomination=snoozer (Retrieved from the Internet on Aug. 5, 2024 )(2 pages total).*
CPVO.*

* cited by examiner

*Primary Examiner* — Susan McCormick Ewoldt
(74) *Attorney, Agent, or Firm* — C. Anne Whealy

(57) ABSTRACT

A new and distinct cultivar of *Phalaenopsis* plant named 'Snoozer', characterized by its upright plant habit; moderately vigorous to vigorous growth habit; strong flowering stems; strong leaves; freely flowering habit with typically three inflorescences developing per plant, each inflorescence with numerous flowers; flowers with white-colored petals with large, irregular and random dark purplish red-colored blotches; and good postproduction longevity.

2 Drawing Sheets

Figure 1:
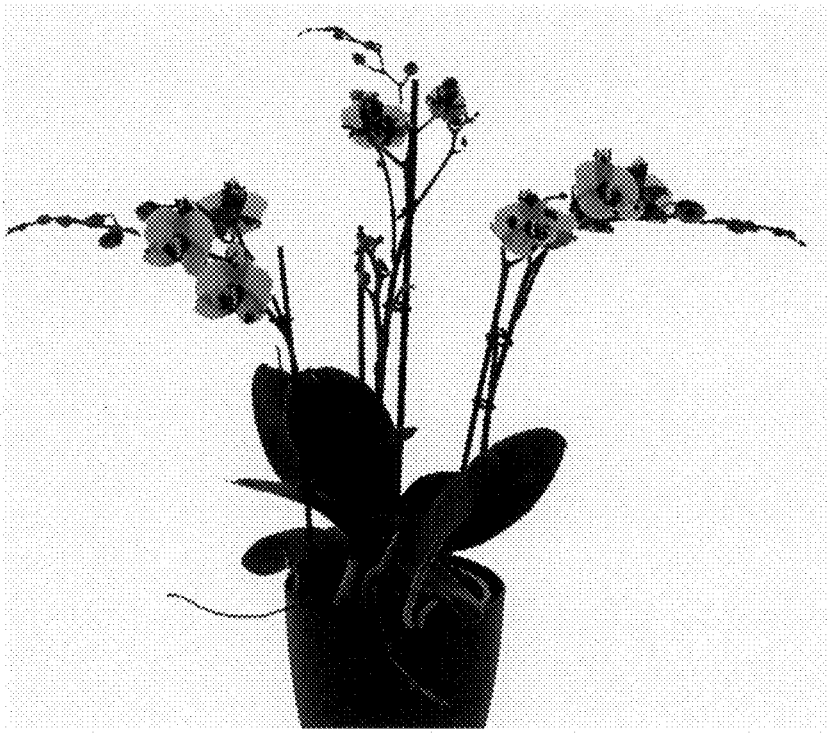

Botanical designation: *Phalaenopsis hybrida.*
Cultivar denomination: 'SNOOZER'.

STATEMENT REGARDING PRIOR DISCLOSURES BY INVENTOR AND APPLICANT/ASSIGNEE

An European Community Plant Breeder's Rights application for the instant plant was filed by the Applicant/Assignee of the instant application, Floricultura B. V. of Heemskerk, The Netherlands on Feb. 27, 2023, application number 2023/0528. Foreign priority is not claimed to this application.

The Inventor and Applicant/Assignee assert that no sales, offers for sale or public distribution of the instant plant occurred more than one year prior to the effective filing date of this application.

Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosures and/or sales prior to the filing date but less than one year prior to the effective filing date.

BACKGROUND OF THE INVENTION

The present invention relates to a new and distinct cultivar of *Phalaenopsis* plant, botanically known as *Phalaenopsis hybrida*, and hereinafter referred to by the name 'Snoozer'.

The new *Phalaenopsis* plant is a product of a planned breeding program conducted by the Inventor in Nantou, Taiwan and Heemskerk, The Netherlands. The objective of the breeding program is to develop new fast-growing and freely flowering *Phalaenopsis* plants with good leaf shape and flowers with unique and attractive patterns and coloration.

The new *Phalaenopsis* plant originated from a cross-pollination in January 2013 in Nantou, Taiwan of *Phalaenopsis hybrida* 'Nankung 4.55 PM', not patented, as the female, or seed, parent with *Phalaenopsis hybrida* 'Harck Galaxy', not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in October 2019.

Asexual reproduction of the new *Phalaenopsis* plant by in vitro meristem propagation in a controlled environment in Assendelft, The Netherlands since October 2020 has shown that the unique features of this new *Phalaenopsis* plant are stable and reproduced true to type in successive generations.

SUMMARY OF THE INVENTION

Plants of the new *Phalaenopsis* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Snoozer'. These characteristics in combination distinguish 'Snoozer' as a new and distinct *Phalaenopsis* plant:

1. Upright plant habit.
2. Moderately vigorous to vigorous growth habit.
3. Strong flowering stems.
4. Strong leaves.
5. Freely flowering habit with typically three inflorescences developing per plant, each inflorescence with numerous flowers.
6. Flowers with white-colored petals with large, irregular and random dark purplish red-colored blotches.
7. Good postproduction longevity.

Plants of the new *Phalaenopsis* can be compared to plants of the female parent, 'Nankung 4.55 PM'. Plants of the new *Phalaenopsis* differ primarily from plants of 'Nankung 4.55 PM' in petal color as petals of plants of the new *Phalaenopsis* have fewer blotches than petals of plants of 'Nankung 4.55 PM'. In addition, the petals of plants of the new *Phalaenopsis* are imbricate whereas the petals of plants of 'Nankung 4.55 PM' are "free" and not imbricate.

Plants of the new *Phalaenopsis* can be compared to plants of the male parent, 'Harck Galaxy'. Plants of the new *Phalaenopsis* differ primarily from plants of 'Harck Galaxy' in petal color as petals of plants of the new *Phalaenopsis* have fewer blotches than petals of plants of 'Harck Galaxy'. In addition, the petals of plants of the new *Phalaenopsis* are imbricate whereas the petals of plants of 'Harck Galaxy' are "free" and not imbricate.

Plants of the new *Phalaenopsis* can be compared to plants of *Phalaenopsis hybrida* 'Crossroads', not patented. In side-by-side comparisons, plants of the new *Phalaenopsis* differ primarily from plants of 'Crossroads' in the following characteristics:

1. Plants of the new *Phalaenopsis* are shorter than plants of 'Crossroads'.
2. Flowers of plants of the new *Phalaenopsis* are not as broad as flowers of plants of 'Crossroads'.
3. Petals of plants of the new *Phalaenopsis* are imbricate whereas the petals of plants of 'Crossroads' are "free" and not imbricate.
4. Peduncles of plants of the new *Phalaenopsis* do not produce anthocyanin whereas peduncles of plants of 'Crossroads' produce anthocyanin.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'Snoozer' grown in a container.

Figure 2:
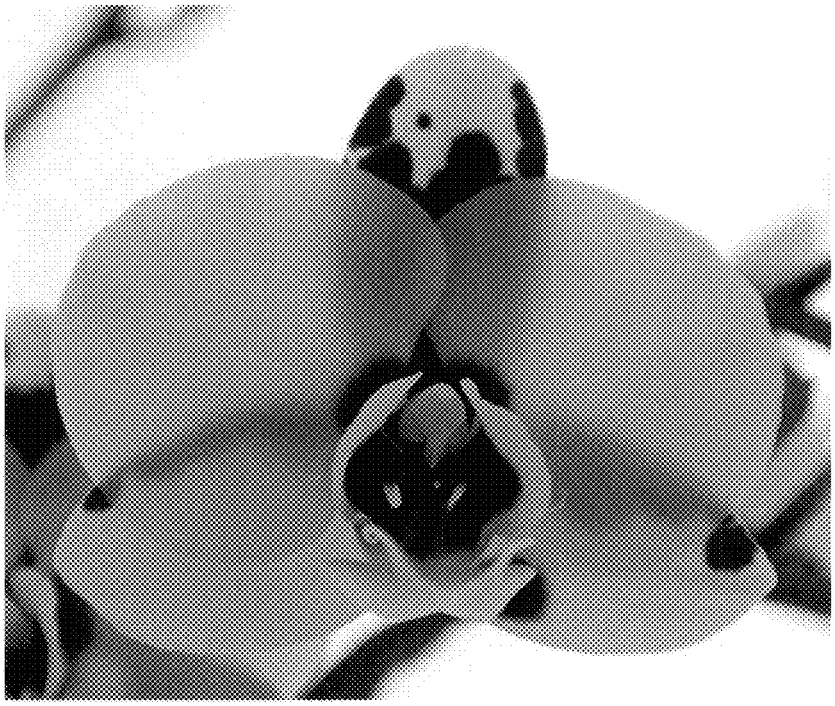

The photograph on the second sheet (FIG. 2) is a close-up view of a typical flower of 'Snoozer'.

DETAILED BOTANICAL DESCRIPTION

The aforementioned photographs and following observations and measurements describe plants grown during the late winter in 11-cm containers in a glass-covered greenhouse in Heemskerk, The Netherlands and under cultural practices typically used in commercial *Phalaenopsis* production. Plants were 18 months old when the photographs and description were taken. During the first twelve months of production of the plants, day and night temperatures averaged 27° C. During the final six months of production of the plants, day temperatures ranged from 20° C. to 22° C. and night temperatures ranged from 18° C. to 20° C. During the production of the plants, light levels ranged from a minimum of 5,000 lux to a maximum of 10,000 lux. In the following description, color references are made to The Royal Horticultural Society Colour Chart, 2015 Edition, except where general terms of ordinary dictionary significance are used.

Botanical classification: *Phalaenopsis hybrida* 'Snoozer'.

Parentage:

*Female, or seed, parent.*—*Phalaenopsis hybrida* 'Nankung 4.55 PM', not patented.

*Male, or pollen, parent.*—*Phalaenopsis hybrida* 'Harck Galaxy', not patented.

Propagation:

*Type.*—By in vitro meristem propagation.

*Time to initiate roots, summer and winter.*—About two weeks at temperatures about 28° C. to 30° C.

*Time to produce a rooted young plant, summer and winter.*—About 20 to 25 weeks at temperatures about 28° C. to 30° C.

*Root description.*—Thin, fibrous; typically light yellowish white in color; actual color of the roots is dependent on substrate composition, water quality, fertilizer, substrate temperature and age of roots.

*Rooting habit.*—Freely branching; medium density.

Plant description:

*Plant form and growth habit.*—Herbaceous epiphyte; upright plant habit with typically three inflorescences developing per plant, each inflorescence with numerous flowers; monopodial; moderately vigorous to vigorous growth habit and moderate growth rate.

*Plant height, substrate level to top of foliar plane.*—About 15.1 cm.

*Plant height, substrate level to top of floral plane.*—About 29.1 cm.

*Plant diameter or spread.*—About 31.9 cm.

Leaf description:

*Arrangement and quantity.*—Distichous, simple; sessile; about five fully-developed leaves per plant.

*Length.*—About 13.1 cm.

*Width.*—About 6.9 cm.

*Aspect.*—Semi-erect.

*Shape.*—Obovate to broadly elliptic; slightly carinate.

*Apex.*—Unequal rounded.

*Base.*—Sheathing. Sheath length: About 1.5 cm. Sheath width: About 1.3 cm. Sheath color: Close to 143C with margins, close to 137B.

*Margin.*—Entire; not undulate.

*Texture and luster, upper surface*.—Smooth, glabrous; moderately glossy.

*Texture and luster, lower surface*.—Smooth, glabrous; slightly glossy.

*Venation pattern*.—Camptodromous.

*Color*.—Developing leaves, upper surface: Close to 137B. Developing leaves, lower surface: Close to a blend of 137B and 146A; towards the base, strongly tinged with close to 187A to 187C; narrow edges, close to 145A and 145B. Fully expanded leaves, upper surface: Close to NN137B; venation, close to NN137A. Fully expanded leaves, lower surface: Close to 146C; towards the margins, close to 146B; venation, close to 144A and 144B.

Inflorescence description:

*Appearance and flowering habit*.—Showy zygomorphic flowers arranged on axillary simple or branched racemes; typically three inflorescences develop per plant; each inflorescence with about 20 flowers; flowers face outwardly on outwardly arching inflorescences supported by upright peduncles; flowers with three petals, two lateral petals and one center petal transformed into a labellum and three sepals.

*Fragrance*.—None detected.

*Time to flower*.—Plants begin flowering about six months after planting; plants flower naturally during the winter into the spring.

*Flower longevity*.—Long flowering period, individual flowers maintain good substance for about six weeks on the plant; flowers not persistent.

*Inflorescence length* (*lowermost flower to inflorescence apex*).—About 20.7 cm.

*Inflorescence width*.—About 11.2 cm.

*Flower buds*.—Height: About 1.5 cm. Diameter: About 1.1 cm by 1.2 cm. Shape: Broadly ovate. Color: Close to 150C with blotches, close to N186C and 187A.

*Flower size*.—About 4.5 cm (vertical) by 5.4 cm (horizontal).

*Flower depth*.—About 2.1 cm.

*Petals, quantity and arrangement*.—Three, two lateral petals and one center petal transformed into a labellum.

*Lateral petals*.—Length: About 2.5 cm. Width: About 2.9 cm. Shape: Roughly reniform. Apex: Rounded. Margin: Entire; not undulate. Texture and luster, upper and lower surfaces: Smooth, glabrous; velvety; matte. Color: When opening, upper surface: Close to NN155D; random and irregular blotches, close to N79B and N79C; at the base, close to N79B and N79C. When opening, lower surface: Close to NN155D; random and irregular blotches visible from upper surface, close to 187A; at the base, close to 187B. Fully opened, upper surface: Close to NN155C; random and irregular blotches, close to N79B and N79C; at the base, close to N79B and N79C. Fully opened, lower surface: Close to NN155C; random and irregular blotches visible from upper surface, close to 187A; at the base, close to 187B.

*Labella*.—Appearance: Three-parted with two lateral lobes and a central lobe. Length, lateral lobes: About 1.5 cm. Width, lateral lobes: About 1.2 cm. Length, central lobe: About 1.5 cm. Width, central lobe: About 0.5 cm to 1.5 cm. Length, cirrhose tips: About 1.1 cm. Shape, lateral lobes: Broadly obovate. Shape, central lobe: Deltoid with a slightly elongate apex. Apex, lateral lobes: Obtuse. Apex, central lobe: Acute with two upward and backwardly curled cirrhose tips. Margins, lateral and central lobes: Entire. Texture and luster, lateral and central lobes, upper and lower surfaces: Smooth, glabrous, moderately velvety; matte. Callosities: Located at the base of the labellum and attachment point of the lateral petals; about 3 mm in length, about 3.5 mm in width and about 3 mm in height. Color: When opening and fully opened, upper surface: Lateral lobes: Close to NN155D; lower margins, close to 4C; at the base, close to N79B and N79C. Central lobe: Close to NN155D; towards the base, close to 4C and at the base, close to N186C; cirrhose tips, close to NN155D. When opening and fully opened, lower surface: Lateral lobes: Close to NN155D; lower margins, close to 4C; at the base, close to 187A and N79C. Central lobe: Close to NN155B; towards the base, close to 4C and at the base, close to N186C; cirrhose tips, close to NN155B. Callosities: When developing, inner and outer surfaces: Close to 165A and laterally, close to 165D. Fully developed, inner and outer surfaces: Close to 165A and laterally, close to 165D.

*Sepals*.—Quantity and arrangement: Three, one upper dorsal sepal and two lower lateral sepals. Length, dorsal sepal: About 2.6 cm. Width, dorsal sepal: About 1.6 cm. Length, lateral sepals: About 2.7 cm. Width, lateral sepals: About 1.8 cm. Shape, dorsal sepal: Obovate. Shape, lateral sepals: Ovate. Apex, dorsal sepal: Obtuse. Apex, lateral sepals: Broadly acute. Base, dorsal and lateral sepals: Truncate. Margins, dorsal and lateral sepals: Entire; not undulate. Texture and luster, dorsal and lateral sepals, upper and lower surfaces: Smooth, glabrous; moderately velvety; matte. Color, dorsal sepal: When opening, upper surface: Close to NN155D; random and irregular blotches, close to 187A and 187B; at the base, close to N186C; venation, close to N186C. When opening, lower surface: Close to NN155A; random and irregular blotches, close to N79A, N79B and N186C; at the base, close to N186C. Fully opened, upper surface: Close to NN155C; random and irregular blotches, close to N79B and N79C; at the base, close to N79B and N79C. Fully opened, lower surface: Close to NN155C; random and irregular blotches visible from upper surface, close to N79B; at the base, close to N79B. Color, lateral sepals: When opening, upper surface: Close to NN155A; towards the base, close to 155A; random and irregular blotches, close to N79A, N79B and N79C; at the base, close to N186C. When opening, lower surface: Close to NN155A; towards the base, close to 157A; random and irregular blotches, close to N186C; at the base, close to N186C. Fully opened, upper surface: Close to NN155C; random and irregular blotches, close to N79B and N79C; at the base, close to N79B and N79C. Fully opened, lower surface: Close to NN155C; random and irregular blotches visible from upper surface, close to N79B; at the base, close to N79B.

*Peduncles*.—Length: About 34.4 cm. Diameter: About 4 mm. Strength: Strong. Aspect: Upright to outwardly arching. Texture and luster: Smooth, glabrous; matte. Color: Close to 148A marbled and densely covered with fine dots, close to 138B.

*Pedicels*.—Length: About 3 cm. Diameter: About 2 mm. Strength: Moderately strong. Aspect: About 50° from peduncle axis. Texture and luster: Smooth, glabrous; matte. Color: Close to 157B; proximally, close to 200B; occasionally tinged with close to 186A and 186B.

*Reproductive organs*.—Androecium: Column length: About 7 mm. Column width: About 5 mm. Column color: Close to N78C and N78D; distally, close to NN155B. Pollinia quantity: Two. Pollinia diameter (per two pollinia): About 2 mm. Pollinia color: Close to 23A. Gynoecium: Stigma length: About 3 mm. Stigma width: About 4 mm. Stigma shape: Reniform. Stigma color: Close to 76C. Ovary length: About 1 cm. Ovary diameter: About 1 mm. Ovary color: Close to 147C. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'Snoozer' as herein illustrated and described.

* * * * *